US006475206B1

(12) United States Patent
Hama et al.

(10) Patent No.: US 6,475,206 B1
(45) Date of Patent: Nov. 5, 2002

(54) LIQUID CONTAINER

(75) Inventors: Yoshihisa Hama, Osaka (JP); Masakazu Mameta, Osaka (JP); Takamitsu Okawara, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/719,105

(22) PCT Filed: Mar. 31, 2000

(86) PCT No.: PCT/JP00/02145

§ 371 (c)(1), (2), (4) Date: Dec. 8, 2000

(87) PCT Pub. No.: WO00/61063

PCT Pub. Date: Oct. 19, 2000

(30) Foreign Application Priority Data

Apr. 9, 1909 (JP) .......................................... 11-103109

(51) Int. Cl.[7] ............................................ A61B 19/00

(52) U.S. Cl. ....................... 604/411; 604/403; 604/412; 604/413; 604/414

(58) Field of Search ................................ 604/403, 411, 604/412, 413, 414

(56) References Cited

U.S. PATENT DOCUMENTS 4,020,839 A * 5/1977 Klapp ........................ 604/414
4,529,095 A * 7/1985 Hansen ........................ 215/531
5,873,872 A * 2/1999 Thibault et al. ............ 604/403
5,890,610 A * 4/1999 Jansen et al. ............... 215/253
6,003,566 A * 12/1999 Thibault et al. .............. 141/25
6,139,534 A * 10/2000 Niedospial et al. .......... 604/403
6,258,078 B1 * 7/2001 Thilly ........................ 206/363
6,382,442 B1 * 5/2002 Thibault et al. ............ 215/247

FOREIGN PATENT DOCUMENTS

JP 8-71122 3/1996

* cited by examiner

*Primary Examiner*—William C. Doerrler
*Assistant Examiner*—Philip Zec
(74) *Attorney, Agent, or Firm*—Kubovcik & Kubovcik

(57) ABSTRACT

There is provided a liquid container capable of transferring liquids germ free in a simple manner within a short period of time and with inconsiderable solution remaining after transfer. The liquid container includes a vessel main body 1, a mouth portion 11 of which is closed by an easily breakable closing member 12, and a hollow needle member 2 crowned pivotably on the mouth portion 11 of the container main body 1. The closing member 12 is provided with a flat knob portion 121. A knob-containing portion 22 of the hollow needle member 2 is provided with a protrusion 24 for joining the knob portion 121 when the hollow needle member 2 is pivoted.

8 Claims, 4 Drawing Sheets

LIQUID CONTAINER

TECHNICAL FIELD

The present invention relates to a liquid container. Particularly, the present invention relates to a liquid container suitable for transferring chemicals germ free from one container to another container.

BACKGROUND OF THE INVENTION

Conventionally, a drug having a disadvantage such as losing its effectiveness by mutual reaction with another component of a mixture with which the drug is preserved in a mixed state, or a drug which is decomposed, denatured or the like by heat during a sterilization treatment such as high pressure vapor sterilization, is generally contained and preserved in a vial or the like hermetically sealed with a rubber plug. Further, these drugs, for administration to a patient, are used by taking out the drugs from the drug containers using a syringe or the like and mixing and injecting them into a transfusion vessel. However, according to such a transfer operation using a syringe, a significant operation time period is taken and, further, there is a concern of contaminating the drug solution.

Hence, in order to resolve the drawbacks of the transfer operation using a syringe, there have been proposed various chemical containers with communication means arranged in each of two containers such that rubber plugs thereof oppose each other and are pierced by a piercing needle of a two headed needle to enable liquids in the two containers to communicate and to transfer chemicals (Japanese Patent Laid-Open No. 71122/1996 and the like).

However, according thereto, transfer of chemicals is carried out by natural flow down through a chemical flow path of the two headed needle and, therefore, the transfer time period is long and, further, there is a concern that the chemicals remain therein.

The present invention has been carried out in view of the above-described situation and it is an object thereof to provide a chemical container capable of transferring chemicals in a short time period germ free by a simple operation and wherein the solution remaining after transfer is inconsiderable.

DISCLOSURE OF THE INVENTION

The inventors conceived that means for closing a mouth portion of a container main body is constituted by a closing member of a twist-off type in place of a rubber plug as a result of an intensive study in order to resolve the above-described problem and completed the invention. That is, according to an aspect of the invention, there is provided a liquid container comprising a container main body, a mouth portion of which is closed by a closing member which is easily breakable and has a flat knob portion, and a hollow needle member pivotably and hermetically crowned on the mouth portion of the container main body. The hollow needle member further comprises joining means for joining the knob portion when the hollow needle member is pivoted, at a position of the hollow needle member containing the knob portion.

Here, it is preferable that a connecting portion which connects the mouth portion and the closing member is formed to be brittle. Further, it is preferable that the hollow needle member is constituted by a needle portion, a knob-containing portion and a skirt portion, and it is more preferable that a space between the skirt portion and the container main body is sealed with a packing. The hollow needle member may be provided with an annular engaging projection at a lower end of the skirt portion and may engage an undercut provided at an outer wall of the mouth portion of the container main body when the needle member is crowned thereon.

BEST MODE FOR CARRYING OUT THE INVENTION

In order to describe the present invention in further detail, an explanation will be given thereof with reference to the attached drawings.

Figure 1:
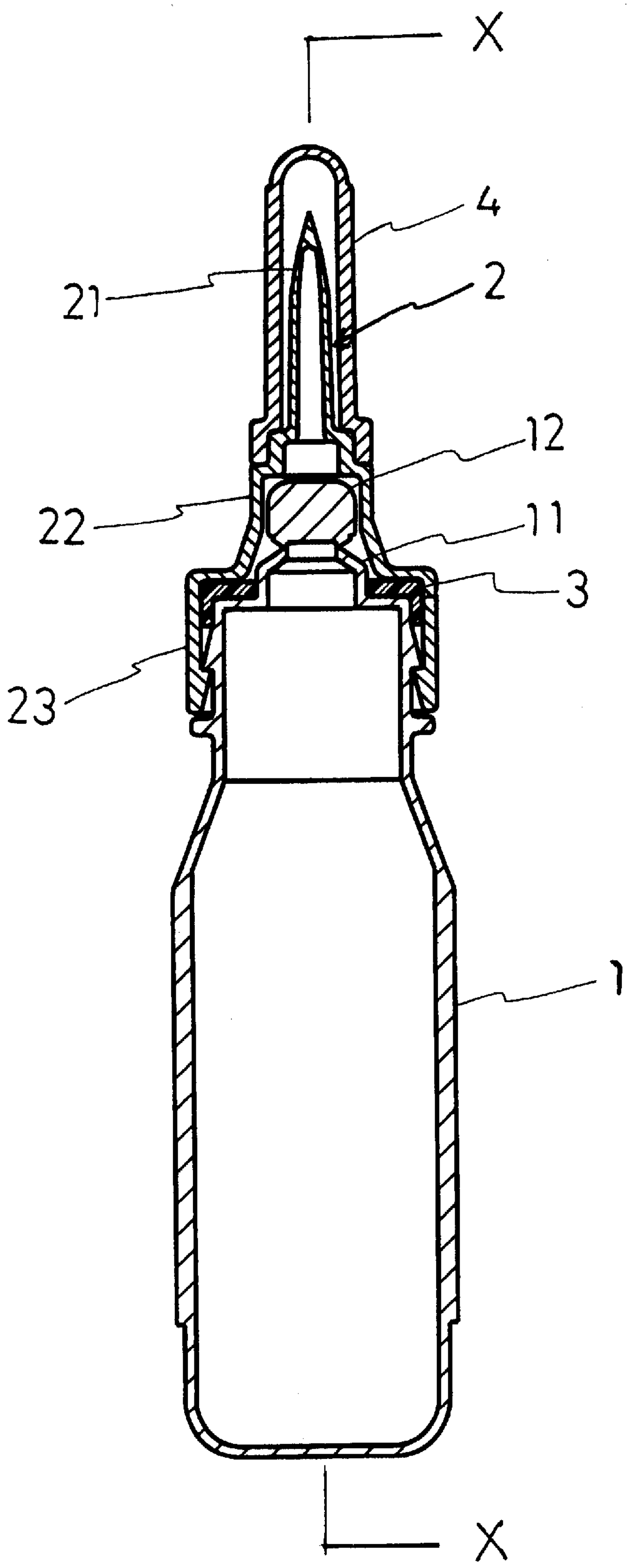
FIG. 1 is a longitudinal sectional view showing an embodiment of the present invention.
Figure 2:
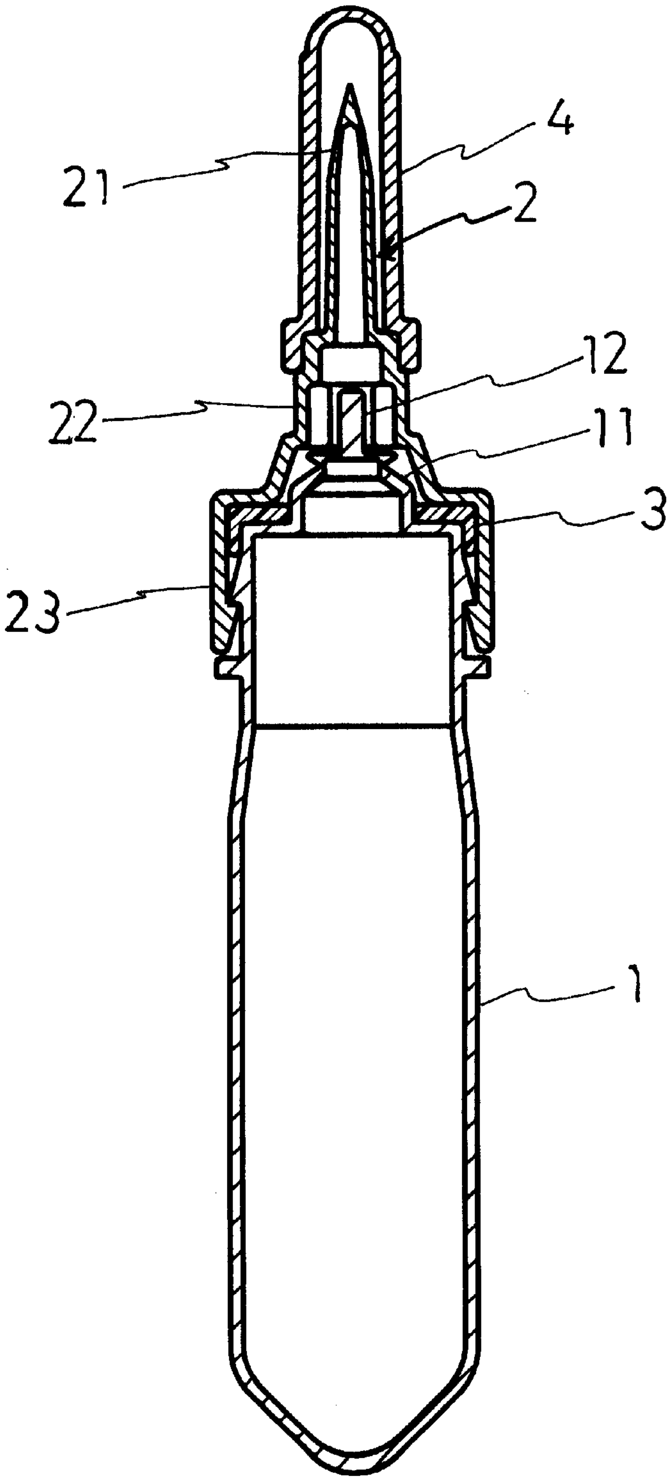
FIG. 2 is a sectional view taken along a line X—X of the liquid container shown in FIG. 1.
Figure 3:
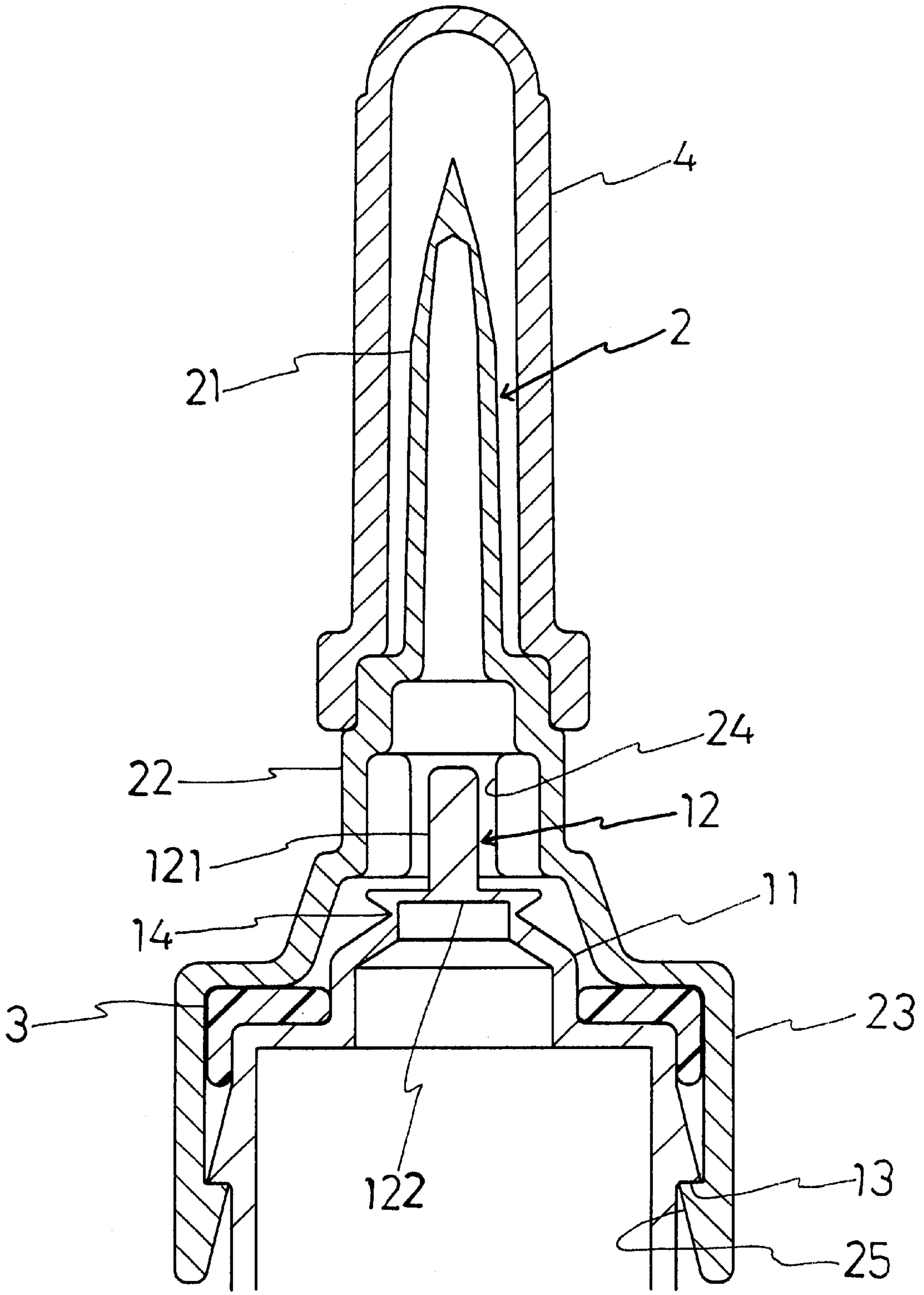
FIG. 3 is an enlarged view of essential portions of FIG. 2.

As shown in FIG. 1 through FIG. 3, a liquid container according to the invention includes a container main body 1, a mouth portion 11 of which is closed by a closing member 12 which is easily breakable, and a hollow needle member 2 crowned pivotably on the mouth portion 11 of the container main body 1. The closing member 12 is provided with a flat knob portion 121 and a protrusion 24 is provided at a knob-containing portion 22 of the hollow needle member 2 for joining the knob portion 121 when the hollow needle member 2 is pivoted. Further, in the drawings, numeral 4 designates a cap for protecting needle portion 21 of the hollow needle member 2.

The container main body 1 is a vessel for containing a liquid such as a chemical inside thereof and is normally formed in a cylindrical shape and made from a flexible resin having chemical resistance such as polyethylene, polypropylene, polyester or the like. An undercut 13 is provided at an outer wall of the mouth portion 11 of the container main body 1 in the peripheral direction and when the hollow needle member 2, described below, is crowned thereon, an engaging projection 25 of the hollow needle member 2 is pivotably engaged therewith. A front end of the mouth portion 11 which is opposed to the undercut 13 is tapered in a stepped shape to form a brittle portion 14 and a closing member 12 is connected easily breakably to the container main body 1 via the brittle portion 14. The closing member 12 is constituted by the flat knob portion 121 and a closing portion 122 for closing the mouth portion 11 of the container main body 1, and when the closing member 12 is rotated around a center axis of the container main body 1, the closing member 12 is broken from the mouth portion 11 at the brittle portion 14.

The hollow needle member 2 is pivotably and hermetically crowned on the mouth portion 11 of the container main body 1, and is generally formed in a hollow shape from a transparent thermoplastic resin such as high density polyethylene or polypropylene, polyester, ABS resin, polycarbonate, polysulfone or the like.

The hollow needle member 2 is constituted by the needle portion 21 comprising a hollow piercing needle, the knob-containing portion 22 which is provided with a space for containing the knob portion 121 of the closing member 12 and a skirt portion 23 hermetically crowned on the outer wall of the mouth portion 11 and is provided with a packing 3 between the skirt portion 23 and the container main body 1 for hermetically sealing both members. Further, protrusion 24 is provided at an inner wall of the knob-containing portion 22 in the longitudinal direction as a joining means for joining the knob portion 121 of the closing member 12 when the hollow needle member 2 is rotated around the center axis. Further, engaging projection 25 is provided for pivotably engaging with the undercut 13 of the outer wall of the mouth portion 11 when the hollow needle member 2 is crowned on the mouth portion 11 of the container main body 1.

Further, although one or a plurality of the protrusion 24 can be used, normally, it is preferable to provide two pairs or a total of four protrusions thereof with a width slightly larger than the thickness of the knob portion 121 so as to contain the knob portion 121. Additionally, although the number of the engaging projection 25 is not particularly restricted, normally, the engaging projection 25 is formed in an annular shape and three to five protrusions thereof may be provided at equal intervals.

Figure 4:
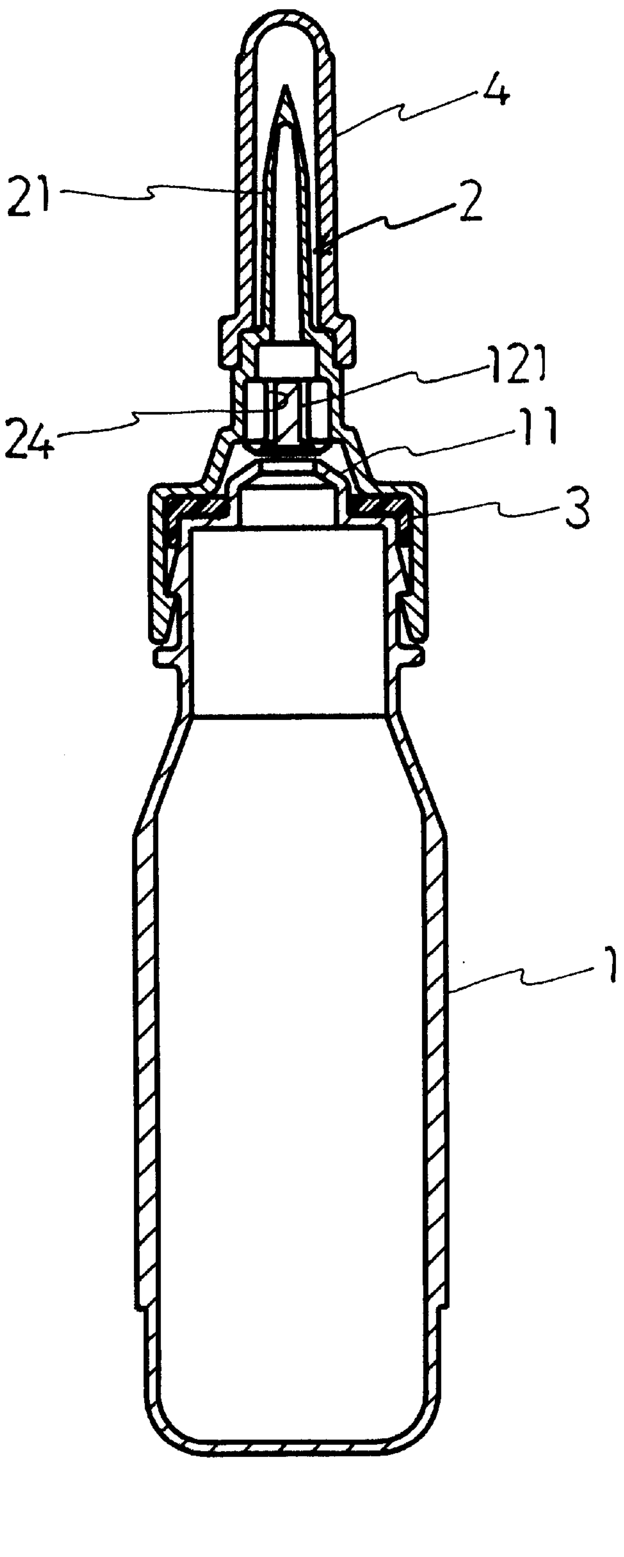
FIG. 4 is a view showing a state in which the closing member is broken by pivoting the hollow needle member of the liquid container shown in FIG. 1.

In using the liquid container according to the invention containing a liquid (normally, a chemical) inside thereof, as shown in FIG. 1, the hollow needle member 2 may be rotated around the center axis in such a state that the hollow needle member 2 is insertingly attached to the cap 4. When the hollow needle member 2 is rotated, the knob portion 121 of the container main body 1 joins with the protrusion 24 of the hollow needle member 2 and rotates together and the container main body 1 is broken from the mouth portion 11 (refer to FIG. 4). When the mouth portion 11 is opened, the cap 4 is detached and the needle portion 21 of the hollow needle member 2 is pierced into a rubber plug of another container (not illustrate) to thereby enable transfer of chemicals contained inside.

INDUSTRIAL APPLICABILITY

As is apparent from the above explanation, chemicals can be transferred germ free in a simple manner and within a short period of time using a liquid container according to the invention. Further, a rubber plug is not used in the liquid container and accordingly, solution remaining after transfer is inconsiderable

What is claimed is:

1. A liquid container comprising a container main body, a mouth portion of which is closed by a closing member easily breakable and having a flat knob portion, and a hollow needle member pivotably and hermetically crowned on the mouth portion of the container main body, wherein the container comprises a joining means for joining the knob portion at a position of the hollow needle member for containing the knob portion when the hollow needle member is pivoted.

2. The liquid container according to claim 1, wherein the mouth portion and the closing member are hermetically connected at a brittle portion.

3. The liquid container according to claim 1, wherein the hollow needle member comprises a needle portion, a knob-containing portion and a skirt portion a space between the skirt portion and the container main body is sealed by a packing.

4. The liquid container according to claim 1, wherein an undercut is provided at an outer wall of the mouth portion of the container main body for engaging with an annular engaging projection provided at a lower end of the skirt portion of the hollow needle member.

5. The liquid container according to claim 2, wherein the hollow needle member comprises a needle portion, a know-containing portion and a skirt portion and a space between the skirt portion and the container main body is sealed by a packing.

6. The liquid container according to claim 2, wherein an undercut is provided at an outer wall of the mouth portion of the container main body for engaging with an annular engaging projection provided at a lower end of the skirt portion of the hollow needle member.

7. The liquid container according to claim 3, wherein an undercut is provided at an outer wall of the mouth portion of the container main body for engaging with an annular engaging projection provided at a lower end of the skirt portion of the hollow needle member.

8. The liquid container according to claim 5, wherein an undercut is provided at an outer wall of the mouth portion of the container main body for engaging with an annular engaging projection provided at a lower end of the skirt portion of the hollow needle member.

* * * * *

UNITED STATES PATENT AND TRADEMARK OFFICE

CERTIFICATE OF CORRECTION

PATENT NO. : 6,475,206 B1
DATED : November 5, 2002
INVENTOR(S) : Yoshihisa Hama et al.

It is certified that error appears in the above-identified patent and that said Letters Patent is hereby corrected as shown below:

Title page,
Item [30], Foreign Application Priority Data, "Apr. 9, 1909" should read -- Apr. 9, 1999 --.

Signed and Sealed this

Twenty-fifth Day of February, 2003

JAMES E. ROGAN
*Director of the United States Patent and Trademark Office*